United States Patent
Zhang et al.

(10) Patent No.: US 9,784,658 B2
(45) Date of Patent: Oct. 10, 2017

(54) METHOD AND DEVICE FOR DETECTING CONCENTRATION OF TINY PARTICULATES IN AIR SAMPLE

(71) Applicant: SHARP KABUSHIKI KAISHA, Osaka-shi, Osaka (JP)

(72) Inventors: Tong Zhang, Shanghai (CN); Yu Liu, Shanghai (CN); Haopeng Li, Shanghai (CN)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 83 days.

(21) Appl. No.: 14/911,650

(22) PCT Filed: Aug. 7, 2014

(86) PCT No.: PCT/JP2014/004121
§ 371 (c)(1),
(2) Date: Feb. 11, 2016

(87) PCT Pub. No.: WO2015/025495
PCT Pub. Date: Feb. 26, 2015

(65) Prior Publication Data
US 2016/0195462 A1 Jul. 7, 2016

(30) Foreign Application Priority Data
Aug. 20, 2013 (CN) .......................... 2013 1 0363270

(51) Int. Cl.
*G01N 1/00* (2006.01)
*G01N 15/06* (2006.01)
(Continued)

(52) U.S. Cl.
CPC .......... *G01N 15/06* (2013.01); *G01N 1/2205* (2013.01); *G01N 1/2273* (2013.01); *G01N 1/24* (2013.01);
(Continued)

(58) Field of Classification Search
CPC .................................................. G01N 1/2273
(Continued)

(56) References Cited

FOREIGN PATENT DOCUMENTS

| CN | 102680349 | 9/2012 |
|----|-----------|--------|
| JP | 2011-179862 | 9/2011 |

OTHER PUBLICATIONS

International Search Report for PCT/JP2014/004121, dated Nov. 18, 2014, 3 pages.
(Continued)

*Primary Examiner* — Clayton E LaBalle
*Assistant Examiner* — Kevin Butler
(74) *Attorney, Agent, or Firm* — Steven Reiss (57) ABSTRACT

A device for detecting a concentration of tiny particulates in an air sample is provided. The device comprises: a container that contains the air sample and has an opening; a sealing mechanism that opens or seals the opening; a sensor provided in the container and operative to sense a total concentration of particulates in the air sample within the container; and a controller connected to the sensor and operative to control the sealing mechanism. The controller is configured to: control the sealing mechanism to open the opening and the sensor to sense a first total concentration of particulates; control the sealing mechanism to seal the opening, so as to seal the container for a predetermined time period, and then control the sensor to sense a second total concentration of particulates; calculate a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates; and calculate the concentration of tiny particulates in the air sample based on the first total concentration of particulates
(Continued)

and the ratio of the concentration of tiny particulates to the total concentration of particulates.

20 Claims, 3 Drawing Sheets

(51) Int. Cl.
*G01N 33/00* (2006.01)
*G01N 1/24* (2006.01)
*G01N 1/22* (2006.01)
*G08B 17/117* (2006.01)
*G01N 15/00* (2006.01)

(52) U.S. Cl.
CPC .. *G01N 33/0011* (2013.01); *G01N 2015/0046* (2013.01); *G08B 17/117* (2013.01)

(58) Field of Classification Search
USPC .................................................. 73/31.02
See application file for complete search history.

(56) References Cited

OTHER PUBLICATIONS

Written Opinion of the ISA for PCT/JP2014/004121, dated Nov. 18, 2014, 4 pages.

METHOD AND DEVICE FOR DETECTING CONCENTRATION OF TINY PARTICULATES IN AIR SAMPLE

This application is the U.S. national phase of International Application No. PCT/JP2014/004121 filed 7 Aug. 2014, which designated the U.S. and claims priority to CN Application No. 201310363270.4 filed 20 Aug. 2013, the entire contents of each of which are hereby incorporated by reference.

TECHNICAL FIELD

The present disclosure relates to detection of air quality, and more particularly, to a method, device, sensor and air purifier capable of detecting a concentration of tiny particulates each having an aerodynamic equivalent diameter equal to or smaller than a predetermined value in an air sample.

BACKGROUND ART

With the rapid industrialization and the explosive growth in the number of motor vehicles in recent years, air pollutions become increasingly severe. In China, the concentration of tiny particulates, particularly fine particulates (each having an aerodynamic equivalent diameter equal to or smaller than 2.5 micro meter, also known as PM2.5), as dominant atmospheric pollutants in the atmosphere, has been continued at a high level since early 2013. The hazy weather has significantly increased and people's health and daily lives are in serious danger. There is thus a need for a detection device for detecting concentration of tiny particulates.

Currently, there have been a number of methods for detecting tiny particulates in the air, including for example quartz oscillating microbalance method, beta ray method and light scattering method. Most of these methods require an inertial impactor as a front-end device for separating tiny particulates from larger particulates. As an example, Patent Document CN102680349A discloses a PM2.5 monitoring device equipped with an inertial impactor. Although the inertial impactor works well in size separation, its high cost, large dimension and precise control of air flow rate limit its application in home scenarios.

On the other hand, deposition methods have been used conventionally for detecting size distribution of particulates in liquid phase. As an example, Patent Document JP2011179862 discloses a method for calculating sedimentation velocity of particulates in liquid phase. Although there is also a deposition process for particulates in the air, it is very different from the deposition process in liquid phase. The viscosity of air is much lower than that of liquid and thus the Brownian dispersion in the air cannot be neglected. Since the Brownian dispersion is sensitive to many factors such as concentration gradient, temperature and particulate size, it is difficult to detect the size distribution of suspended particulates in the air precisely using the deposition methods.

SUMMARY OF INVENTION

Technical Problem

It is an object of the present disclosure to provide a method, device, sensor and air purifier for detecting a concentration of tiny particulates each having an aerodynamic equivalent diameter equal to or smaller than a predetermined value in an air sample, capable of detecting the concentration of tiny particulates more precisely without a significant increase in cost.

Solution to Problem

An aspect of the invention provides a device for detecting a concentration of tiny particulates in an air sample, the tiny particulates each having an aerodynamic equivalent diameter equal to or smaller than a predetermined value, the device including:

(a) a container that contains the air sample and has an opening;

(b) a sealing mechanism that opens or seals the opening;

(c) a sensor provided in the container and operative to sense a total concentration of particulates in the air sample within the container; and (d) a controller connected to the sensor and operative to control the sealing mechanism, wherein the controller is configured to:

(i) control the sealing mechanism to open the opening and the sensor to sense a first total concentration of particulates;

(ii) control the sealing mechanism to seal the opening, so as to seal the container for a predetermined time period, and then control the sensor to sense a second total concentration of particulates;

(iii) calculate a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates; and (iv) calculate the concentration of tiny particulates in the air sample based on the first total concentration of particulates and the ratio of the concentration of tiny particulates to the total concentration of particulates.

Another aspect of the invention provides a sensor, including:

(a) a sensing unit having an air path through the sensing unit and operative to sense a concentration of particulates in an air sample within the air path;

(b) a sealing mechanism that opens or seals the air path; and (c) a controller connected to the sensing unit and operative to control the sealing mechanism, wherein the controller is configured to:

(i) control the sealing mechanism to open the air path and the sensing unit to sense a first total concentration of particulates;

(ii) control the sealing mechanism to seal the air path for a predetermined time period, and then control the sensing unit to sense a second total concentration of particulates;

(iii) calculate a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates, the tiny particulates each having an aerodynamic equivalent diameter equal to or smaller than a predetermined value; and (iv) calculate the concentration of tiny particulates in the air sample based on the first total concentration of particulates and the ratio of the concentration of tiny particulates to the total concentration of particulates.

Another aspect of the invention provides a method for detecting a concentration of tiny particulates in an air sample within a container, the tiny particulates each having an aerodynamic equivalent diameter equal to or smaller than a predetermined value, the method including:

(a) sensing an initial first total concentration of particulates in the air sample;

(b) sensing a second total concentration of particulates in the air sample after the container has been sealed for a predetermined time period;

(c) calculating a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates; and (d) calculating the concentration of tiny particulates in the air sample based on the first total concentration of particulates and the ratio of the concentration of tiny particulates to the total concentration of particulates.

Advantageous Effects of Invention

According to a first aspect of the present disclosure, a device for detecting a concentration of tiny particulates in an air sample is provided. The tiny particulates each have an aerodynamic equivalent diameter equal to or smaller than a predetermined value. The device comprises: a container that contains the air sample and has an opening; a sealing mechanism that opens or seals the opening; a sensor provided in the container and operative to sense a total concentration of particulates in the air sample within the container; and a controller connected to the sensor and operative to control the sealing mechanism. The controller is configured to: control the sealing mechanism to open the opening and the sensor to sense a first total concentration of particulates; control the sealing mechanism to seal the opening, so as to seal the container for a predetermined time period, and then control the sensor to sense a second total concentration of particulates; calculate a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates; and calculate the concentration of tiny particulates in the air sample based on the first total concentration of particulates and the ratio of the concentration of tiny particulates to the total concentration of particulates.

In an embodiment, the predetermined relationship is represented as a correction coefficient obtained by: injecting a reference air sample into the container, the reference air sample having a known ratio of the concentration of tiny particulates to the total concentration of particulates; sensing a first total reference concentration of particulates using the sensor; sensing a second total reference concentration of particulates using the sensor after the container has been sealed for the predetermined time period; and calculating the correction coefficient by dividing the known ratio of the concentration of tiny particulates to the total concentration of particulates by the ratio of the second total reference concentration of particulates to the first total reference concentration of particulates.

Preferably, the container further comprises a check valve that is opened while the opening is opened and closed while the opening is sealed. The device further comprises an air pump that pumps air from the container via the check valve while the opening is opened, so as to accelerate entry of air outside the container into the container via the opening and to accelerate dispersion of the particulates within the container.

Preferably, the opening is arranged below the sensor.

Preferably, the predetermined value is 2.5 micro meter.

Preferably, the predetermined time period is 3 minutes.

According to a second aspect of the present disclosure, a sensor is provided. The sensor comprises: a sensing unit having an air path through the sensing unit and operative to sense a concentration of particulates in an air sample within the air path; a sealing mechanism that opens or seals the air path; and a controller connected to the sensing unit and operative to control the sealing mechanism. The controller is configured to: control the sealing mechanism to open the air path and the sensing unit to sense a first total concentration of particulates; control the sealing mechanism to seal the air path for a predetermined time period, and then control the sensing unit to sense a second total concentration of particulates; calculate a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates, the tiny particulates each having an aerodynamic equivalent diameter equal to or smaller than a predetermined value; and calculate the concentration of tiny particulates in the air sample based on the first total concentration of particulates and the ratio of the concentration of tiny particulates to the total concentration of particulates.

In an embodiment, the predetermined relationship is represented as a correction coefficient obtained by: injecting a reference air sample into the air path, the reference air sample having a known ratio of the concentration of tiny particulates to the total concentration of particulates; sensing a first total reference concentration of particulates using the sensing unit; sensing a second total reference concentration of particulates using the sensing unit after the air path has been sealed for the predetermined time period; and calculating the correction coefficient by dividing the known ratio of the concentration of tiny particulates to the total concentration of particulates by the ratio of the second total reference concentration of particulates to the first total reference concentration of particulates.

Preferably, the predetermined value is 2.5 micro meter.

Preferably, the predetermined time period is 3 minutes.

According to a third aspect of the present disclosure, an air purifier is provided. The air purifier comprises the device according to the above first aspect or the sensor according to the above second aspect.

According to a fourth aspect of the present disclosure, a method for detecting a concentration of tiny particulates in an air sample within a container is provided. The tiny particulates each have an aerodynamic equivalent diameter equal to or smaller than a predetermined value. The method comprises: sensing an initial first total concentration of particulates in the air sample; sensing a second total concentration of particulates in the air sample after the container has been sealed for a predetermined time period; calculating a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates; and calculating the concentration of tiny particulates in the air sample based on the first total concentration of particulates and the ratio of the concentration of tiny particulates to the total concentration of particulates.

In an embodiment, the predetermined relationship is represented as a correction coefficient obtained by: injecting a reference air sample into the container, the reference air sample having a known ratio of the concentration of tiny particulates to the total concentration of particulates; sensing a first total reference concentration of particulates; sensing a second total reference concentration of particulates after the container has been sealed for the predetermined time period; and calculating the correction coefficient by dividing the known ratio of the concentration of tiny particulates to the total concentration of particulates by the ratio of the second total reference concentration of particulates to the first total reference concentration of particulates.

Preferably, the method further comprises: using an air pump to accelerate entry of air outside the container into the container while the container is not sealed and to accelerate dispersion of the particulates within the container.

Preferably, the predetermined value is 2.5 micro meter.

Preferably, the predetermined time period is 3 minutes.

With the embodiments of the present disclosure, it is possible to detect the concentration of tiny particulates more precisely without a significant increase in cost.

The above and other objects, features and advantages of the present disclosure will be more apparent from the following preferred embodiments illustrated with reference to the figures, in which:

DESCRIPTION OF EMBODIMENTS

In the following, the embodiments of the present disclosure will be described with reference to the figures, throughout which same reference signs refer to same or similar elements.

The present disclosure is based on the fact that, according to the fundamental aerosol dynamics, the larger a particulate is, the faster it will deposit. Hence, for an air sample within a sealed space, there is a predetermined relationship between a concentration variation of particulates and a ratio of tiny particulates to all particulates in a static deposition process. An approximate estimate of the concentration of tiny particulates can be calculated from such relationship. As used in the present disclosure, a "tiny particulate" refers to a particulate matter having an aerodynamic equivalent diameter equal to or smaller than a predetermined value. As an example, a "tiny particulate" may refer to a particulate matter having an aerodynamic equivalent diameter equal to or smaller than 10 micro meter. Particularly, a "tiny particulate" include a particulate matter having an aerodynamic equivalent diameter equal to or smaller than 2.5 micro meter (PM2.5).

FIGS. 1(a) and 1(b) are schematic diagrams of a device 100 for detecting a concentration of tiny particulates in an air sample according to an embodiment of the present disclosure. FIGS. 1(a) and 1(b) show two operation states of the device 100, respectively. As shown, the device 100 includes: a container 110 that contains the air sample and has an opening; a sealing mechanism 120 that opens or seals the opening; and a sensor 130 provided in the container 110 and operative to sense a total concentration of particulates in the air sample within the container 110. In a preferred embodiment, the opening is arranged below the sensor 130, so as to prevent excessively large particulates in the air outside the container 110 from entering into the container 110, which may otherwise cause interference to the detection result.

The device 100 further includes a controller 140 connected to the sensor 130 and operative to control the sealing mechanism 120.

First, as shown in FIG. 1(a), the controller 140 controls the sealing mechanism 120 to open the opening. At this time, the air sample inside the container is substantially the same as the air outside the container, i.e., they have the same concentration of particulates. The controller 140 controls the sensor 130 to sense a total concentration C1 of particulates (i.e., a total concentration of particulates in the air sample within the container 110 when the opening of the container 110 is opened).

Then, as shown in FIG. 1(b), the controller 140 controls the sealing mechanism 120 to seal the opening, so as to seal the container 110 for a predetermined time period. After that, the controller 140 controls the sensor 130 to sense a total concentration C2 of particulates (i.e., a total concentration of particulates in the air sample within the container 110 after the contained 110 has been sealed for the predetermined time period). In an exemplary embodiment, the above predetermined time period is 3 minutes.

The controller 140 calculates a ratio R of a concentration of tiny particulates to a total concentration of particulates based on a predetermined relationship between the ratio R of the concentration of tiny particulates to the total concentration of particulates and a ratio of the total concentration C2 of particulates to the total concentration C1 of particulates.

Then, the controller 140 calculates the concentration C of tiny particulates in the air sample based on the total concentration C1 of particulates and the ratio R of the concentration of tiny particulates to the total concentration of particulates.

In other words, $$C = C1 \times R \tag{1}$$

In an embodiment, the predetermined relationship can be represented as a correction coefficient n obtained by: injecting a reference air sample into the container 110, the reference air sample having a known ratio r of the concentration of tiny particulates to the total concentration of particulates; sensing an initial total reference concentration c1 of particulates using the sensor 130; sensing a total reference concentration c2 of particulates using the sensor 130 after the container 110 has been sealed for the predetermined time period; and calculating the correction coefficient n by dividing the known ratio r of the concentration of tiny particulates to the total concentration of particulates by the ratio of the total reference concentration c2 of particulates to the total reference concentration c1 of particulates.

In other words, $$n = r/(c2/c1) \quad (2)$$

It is to be noted that the correction coefficient n may be dependent on a number of factors, such as the container 110's shape and size as well as the location of the sensor 130 in the container 110. Thus, it is difficult to calculate the correction coefficient n using a fixed mathematical equation. Rather, with the above experiments, it is possible to obtain n based on Equation (2).

In an embodiment, n can be represented in a form of a lookup table. An exemplary relationship between c2/c1 and n is listed in Table 1 below.

TABLE 1

Lookup Table for Correction Coefficient n

| | c2/c1 | | | | | | | |
|---|---|---|---|---|---|---|---|---|
| | 0-0.1 | 0-0.2 | 0.2-0.3 | 0.3-0.4 | 0.4-0.5 | 0.5-0.6 | 0.6-0.7 | 0.7-0.8 |
| n | 0.8 | 0.82 | 0.85 | 0.9 | 1 | 1.1 | 1.15 | 1.18 |

Specifically, after the correction coefficient n has been obtained, the ratio R of the concentration of tiny particulates to the total concentration of particulates can be calculated as follows:

$$R = n \times (C2/C1) \quad (3)$$

Figure 1:
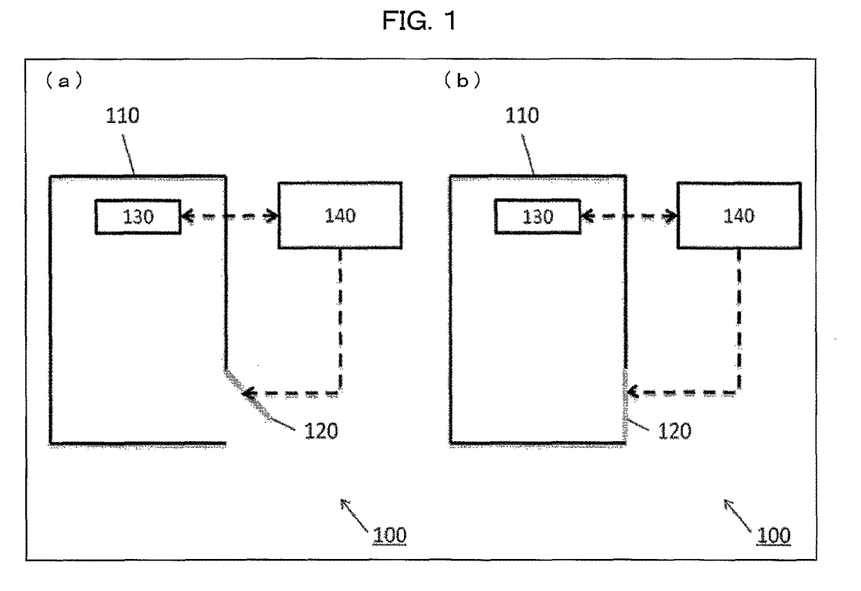
FIGS. 1(a) and 1(b) are schematic diagrams of a device for detecting a concentration of tiny particulates in an air sample according to an embodiment of the present disclosure.

Reference is now made to FIGS. 2(a) and 2(b), which are schematic diagrams of a device 200 for detecting a concentration of tiny particulates in an air sample according to another embodiment of the present disclosure. Like the device 100 shown in FIG. 1, the device 200 includes a container 210, a sealing mechanism 220, a sensor 230 and a controller 240. The configurations and operations of the container 210, sealing mechanism 220, sensor 230 and controller 240 are substantially the same as those of the container 110, sealing mechanism 120, sensor 130 and controller 140 as shown in FIG. 1 and the description thereof will thus be omitted here.

Figure 2:
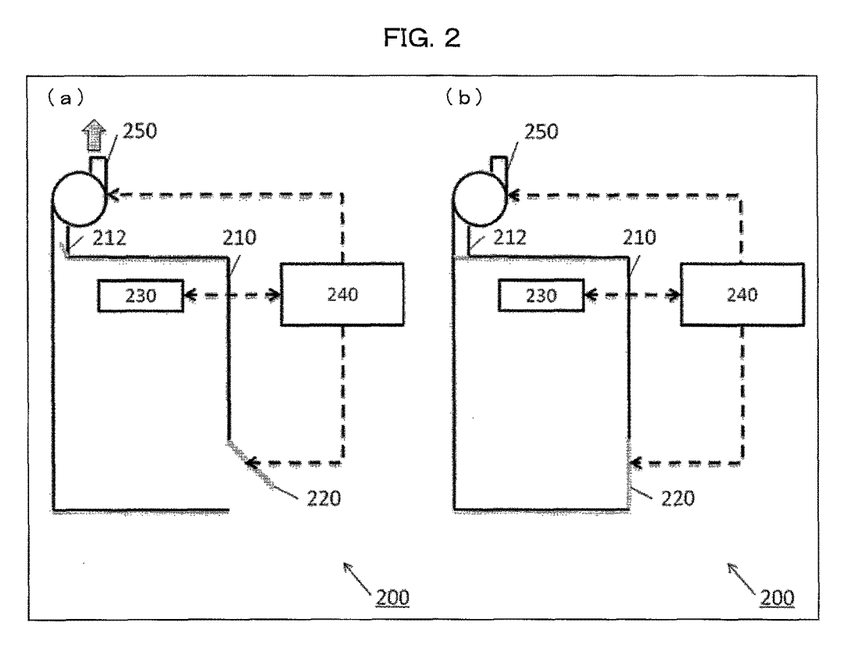
FIGS. 2(a) and 2(b) are schematic diagrams of a device for detecting a concentration of tiny particulates in an air sample according to another embodiment of the present disclosure.

As shown in FIG. 2, the container 210 further includes a check valve 212 that is opened while the opening is opened (as shown in FIG. 2(a)) and closed while the opening is sealed (as shown in FIG. 2(b)). The device 200 further includes an air pump 250 that pumps air from the container 210 via the check valve 212 while the opening is opened, so as to accelerate entry of air outside the container 210 into the container 210 via the opening and to accelerate dispersion of the particulates within the container 210.

Figure 3:
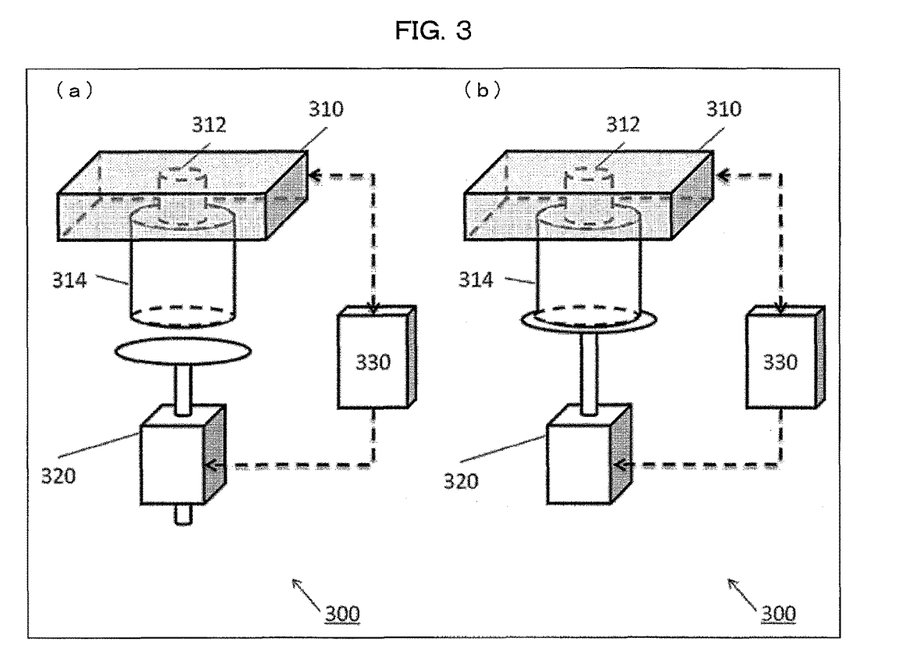
FIGS. 3(a) and 3(b) are schematic diagrams of a sensor according to an embodiment of the present disclosure.

FIGS. 3(a) and 3(b) are schematic diagrams of a sensor 300 according to an embodiment of the present disclosure. As shown, the sensor 300 includes: a sensing unit 310 having an air path 312 through the sensing unit 310 and operative to sense a concentration of particulates in an air sample within the air path 312. The sensor 300 further includes: a sealing mechanism 320 that opens or seals the air path 312. In the embodiment shown in FIG. 3, the air path 312 has one end sealed and the other end connected to one end of a glass tube 314 that contains the air sample. The sealing mechanism 320 is capable of opening or sealing the other end of the glass tube, so as to open or seal the air path 312. As an example, the sealing mechanism 320 can be implemented using an electromagnetic element.

It is to be noted here that the structure shown in FIG. 3 is illustrative only. Both ends of the air path can be opened or sealed by the sealing mechanism 320 (e.g., by providing a sealing mechanism 320 at each end of the air path). The glass tube 314 is optional. Without the glass tube 314, the sealing mechanism 320 can seal the air path 312 directly.

The sensor 300 further includes a controller 330 connected to the sensing unit 310 and operative to control the sealing mechanism 320.

First, as shown in FIG. 3(a), the controller 330 controls the sealing mechanism 320 to open the air path 312 and the sensing unit 310 to sense a total concentration C1 of particulates (i.e., a total concentration of particulates in the air sample within the air path 312 when the air path 312 is opened).

Then, as shown in FIG. 3(b), the controller 330 controls the sealing mechanism 320 to seal the air path 312 for a predetermined time period. After that, the controller 330 controls the sensing unit 310 to sense a total concentration C2 of particulates (i.e., a total concentration of particulates in the air sample within the air path 312 after the air path 312 has been sealed for the predetermined time period). In an exemplary embodiment, the above predetermined time period is 3 minutes.

The controller 330 calculates a ratio R of a concentration of tiny particulates to a total concentration of particulates based on a predetermined relationship between the ratio R of the concentration of tiny particulates to the total concentration of particulates and a ratio of the total concentration C2 of particulates to the total concentration C1 of particulates.

Then, the controller 330 calculates the concentration C of tiny particulates in the air sample, based on the total concentration C1 of particulates and the ratio R of the concentration of tiny particulates to the total concentration of particulates.

In an embodiment, the predetermined relationship can be represented as a correction coefficient n obtained by: injecting a reference air sample into the air path 312, the reference air sample having a known ratio r of the concentration of tiny particulates to the total concentration of particulates; sensing an initial total reference concentration c1 of particulates using the sensing unit 310; sensing a total reference concentration c2 of particulates using the sensing unit 310 after the air path 312 has been sealed for the predetermined time period; and calculating the correction coefficient n by dividing the known ratio r of the concentration of tiny particulates to the total concentration of particulates by the ratio of the total reference concentration c2 of particulates to the total reference concentration c1 of particulates.

More specifically, the correction coefficient n can be obtained based on the above Equation (2) or Table 1. Then, the ratio R of the concentration of tiny particulates to the total concentration of particulates can be calculated based on the above Equation (3). Finally, the concentration C of tiny particulates can be calculated based on the above Equation (1).

According to another embodiment of the present disclosure, an air purifier is provided. The air purifier includes the above device 100, device 200 or sensor 300.

Figure 4:
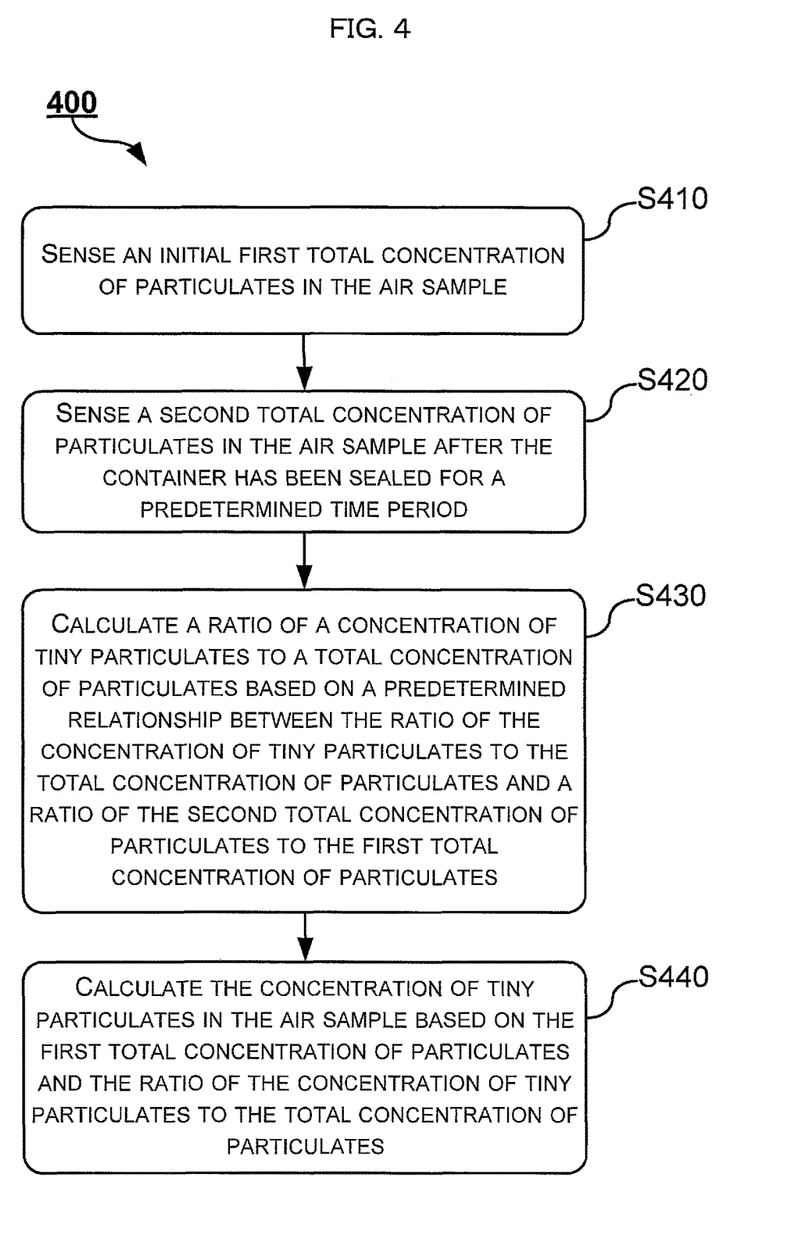
FIG. 4 is a flowchart illustrating a method for detecting a concentration of tiny particulates in an air sample according to an embodiment of the present disclosure.

According to yet another embodiment of the present disclosure, a method 400 for detecting a concentration of tiny particulates in an air sample within a container is provided. The tiny particulates each have an aerodynamic equivalent diameter equal to or smaller than a predetermined value. As shown in FIG. 4, the method 400 includes the following steps.

At step S410, an initial first total concentration of particulates in the air sample is sensed.

At step S420, a second total concentration of particulates in the air sample is sensed after the container has been sealed for a predetermined time period.

At step S430, a ratio of a concentration of tiny particulates to a total concentration of particulates is calculated based on a predetermined relationship between the ratio of the concentration of tiny particulates to the total concentration of particulates and a ratio of the second total concentration of particulates to the first total concentration of particulates.

At step S440, the concentration of tiny particulates in the air sample is calculated based on the first total concentration of particulates and the ratio of the concentration of tiny particulates to the total concentration of particulates.

In an embodiment, the predetermined relationship is represented as a correction coefficient obtained by: injecting a reference air sample into the container, the reference air sample having a known ratio of the concentration of tiny particulates to the total concentration of particulates; sensing a first total reference concentration of particulates; sensing a second total reference concentration of particulates after the container has been sealed for the predetermined time period; and calculating the correction coefficient by dividing the known ratio of the concentration of tiny particulates to the total concentration of particulates by the ratio of the second total reference concentration of particulates to the first total reference concentration of particulates.

Preferably, the method 400 further includes: using an air pump to accelerate entry of air outside the container into the container while the container is not sealed and to accelerate dispersion of the particulates within the container.

Preferably, the predetermined value is 2.5 micro meter.

Preferably, the predetermined time period is 3 minutes.

The present disclosure provides a method, device, sensor and air purifier for detecting a concentration of tiny particulates each having an aerodynamic equivalent diameter equal to or smaller than a predetermined value in an air sample, capable of detecting the concentration of tiny particulates more precisely without a significant increase in cost.

The present disclosure has been described above with reference to the preferred embodiments thereof. It should be understood that various modifications, alternations and additions can be made by those skilled in the art without departing from the spirits and scope of the present disclosure. Therefore, the scope of the present disclosure is not limited to the above particular embodiments but only defined by the claims as attached and the equivalents thereof.

The invention claimed is:

1. A device for detecting a concentration of tiny particulates in an air sample, the tiny particulates each having an aerodynamic equivalent diameter equal to or smaller than a predetermined value, the device comprising:
   (a) a container that contains the air sample and has an opening;
   (b) a sealing mechanism that opens or seals the opening;
   (c) a sensor provided in the container and operative to sense a total concentration of particulates in the air sample within the container; and
   (d) a controller connected to the sensor and operative to control the sealing mechanism,
   wherein the controller is configured to:
      (i) control the sealing mechanism to open the opening and the sensor to sense a first total concentration of particulates;
      (ii) control the sealing mechanism to seal the opening, so as to seal the container for a predetermined time period, and then control the sensor to sense a second total concentration of particulates;
      (iii) calculate a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates; and
      (iv) calculate the concentration of tiny particulates in the air sample based on the first total concentration of particulates and the ratio of the concentration of tiny particulates to the total concentration of particulates.

2. The device of claim 1, wherein the predetermined relationship is represented as a correction coefficient obtained by:
   injecting a reference air sample into the container, the reference air sample having a known ratio of the concentration of tiny particulates to the total concentration of particulates;
   sensing a first total reference concentration of particulates using the sensor;
   sensing a second total reference concentration of particulates using the sensor after the container has been sealed for the predetermined time period; and
   calculating the correction coefficient by dividing the known ratio of the concentration of tiny particulates to the total concentration of particulates by the ratio of the second total reference concentration of particulates to the first total reference concentration of particulates.

3. The device of claim 2, wherein
   the container further comprises a check valve that is opened while the opening is opened and closed while the opening is sealed, and
   the device further comprises an air pump that pumps air from the container via the check valve while the opening is opened, so as to accelerate entry of air outside the container into the container via the opening and to accelerate dispersion of the particulates within the container.

4. The device of claim 1, wherein the opening is arranged below the sensor.

5. The device of claim 1, wherein the predetermined value is 2.5 micro meter.

6. The device of claim 4, wherein the predetermined time period is 3 minutes.

7. A sensor, comprising:
   (a) a sensing unit having an air path through the sensing unit and operative to sense a concentration of particulates in an air sample within the air path;
   (b) a sealing mechanism that opens or seals the air path; and
   (c) a controller connected to the sensing unit and operative to control the sealing mechanism,
   wherein the controller is configured to:
      (i) control the sealing mechanism to open the air path and the sensing unit to sense a first total concentration of particulates;

(ii) control the sealing mechanism to seal the air path for a predetermined time period, and then control the sensing unit to sense a second total concentration of particulates;

(iii) calculate a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates, the tiny particulates each having an aerodynamic equivalent diameter equal to or smaller than a predetermined value; and (iv) calculate the concentration of tiny particulates in the air sample based on the first total concentration of particulates and the ratio of the concentration of tiny particulates to the total concentration of particulates.

8. Theسensor of claim 7, wherein the predetermined relationship is represented as a correction coefficient obtained by:

injecting a reference air sample into the air path, the reference air sample having a known ratio of the concentration of tiny particulates to the total concentration of particulates;

sensing a first total reference concentration of particulates using the sensing unit;

sensing a second total reference concentration of particulates using the sensing unit after the air path has been sealed for the predetermined time period; and calculating the correction coefficient by dividing the known ratio of the concentration of tiny particulates to the total concentration of particulates by the ratio of the second total reference concentration of particulates to the first total reference concentration of particulates.

9. The sensor of claim 7, wherein the predetermined value is 2.5 micro meter.

10. The sensor of claim 7, wherein the predetermined time period is 3 minutes.

11. An air purifier, comprising the device according to claim 1.

12. A method for detecting a concentration of tiny particulates in an air sample within a container, the tiny particulates each having an aerodynamic equivalent diameter equal to or smaller than a predetermined value, the method comprising:

(a) sensing an initial first total concentration of particulates in the air sample;

(b) sensing a second total concentration of particulates in the air sample after the container has been sealed for a predetermined time period;

(c) calculating a ratio of a concentration of tiny particulates to a total concentration of particulates based on a predetermined relationship between the ratio of the concentration of tiny particulates to the total concentration of particulates and a ratio of the second total concentration of particulates to the first total concentration of particulates; and (d) calculating the concentration of tiny particulates in the air sample based on the first total concentration of particulates and the ratio of the concentration of tiny particulates to the total concentration of particulates.

13. The method of claim 12, wherein the predetermined relationship is represented as a correction coefficient obtained by:

injecting a reference air sample into the container, the reference air sample having a known ratio of the concentration of tiny particulates to the total concentration of particulates;

sensing a first total reference concentration of particulates;

sensing a second total reference concentration of particulates after the container has been sealed for the predetermined time period; and calculating the correction coefficient by dividing the known ratio of the concentration of tiny particulates to the total concentration of particulates by the ratio of the second total reference concentration of particulates to the first total reference concentration of particulates.

14. The method of claim 12, further comprising:

using an air pump to accelerate entry of air outside the container into the container while the container is not sealed and to accelerate dispersion of the particulates within the container.

15. The method of claim 12, wherein the predetermined value is 2.5 micro meter.

16. The method of claim 12, wherein the predetermined time period is 3 minutes.

17. The device of claim 1, wherein the container further comprises a check valve that is opened while the opening is opened and closed while the opening is sealed, and the device further comprises an air pump that pumps air from the container via the check valve while the opening is opened, so as to accelerate entry of air outside the container into the container via the opening and to accelerate dispersion of the particulates within the container.

18. The method of claim 13, further comprising: using an air pump to accelerate entry of air outside the container into the container while the container is not sealed and to accelerate dispersion of the particulates within the container.

19. An air purifier, comprising the device according to claim 3.

20. An air purifier, comprising the sensor according to claims 17.

* * * * *